(12) United States Patent
Wirbisky et al.

(10) Patent No.: US 11,406,483 B2
(45) Date of Patent: Aug. 9, 2022

(54) ARTIFICIAL SPHINCTER SYSTEM AND METHOD

(71) Applicant: Boston Scientific Scimed, Inc., Maple Grove, MN (US)

(72) Inventors: Alan G. Wirbisky, Aubrey, TX (US); Andrew P. VanDeWeghe, Grayslake, IL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 277 days.

(21) Appl. No.: 15/797,734

(22) Filed: Oct. 30, 2017

(65) Prior Publication Data

US 2018/0064519 A1 Mar. 8, 2018

Related U.S. Application Data

(63) Continuation of application No. 13/328,856, filed on Dec. 16, 2011, now Pat. No. 9,801,702.

(60) Provisional application No. 61/423,777, filed on Dec. 16, 2010.

(51) Int. Cl.
*A61F 2/00* (2006.01)
(52) U.S. Cl.
CPC .................... *A61F 2/004* (2013.01)
(58) Field of Classification Search
CPC ............ A61F 2/004; A61F 5/005–0066; A61F 2/00–0054; A61F 5/0003–0089; A61F 2/0031–0054
USPC ..................................................... 600/29–32
See application file for complete search history.

(56) References Cited

U.S. PATENT DOCUMENTS

| 3,832,996 A | 9/1974 | Kalnberz et al. |
| 3,893,456 A | 7/1975 | Small |
| 3,987,789 A | 10/1976 | Timm et al. |
| 3,991,752 A | 11/1976 | Gerow et al. |
| 4,066,073 A | 1/1978 | Finney et al. |
| 4,151,840 A | 5/1979 | Barrington et al. |
| 4,151,841 A | 5/1979 | Barrington et al. |
| 4,177,805 A | 12/1979 | Tudoriu et al. |
| 4,187,839 A | 2/1980 | Nuwayser et al. |

(Continued)

FOREIGN PATENT DOCUMENTS

| EP | 0137752 B1 | 8/1989 |
| EP | 0774935 B1 | 11/1999 |

(Continued)

OTHER PUBLICATIONS

W. Small, IV et al., Biomedical applications of thermally activated shape memory polymers, J. Mater. Chem., 2010, 20 , pp. 3356-3366 (Year: 2010).*

(Continued)

*Primary Examiner* — Sunita Reddy
(74) *Attorney, Agent, or Firm* — Brake Hughes Bellermann LLP

(57) ABSTRACT

The present invention provides an artificial sphincter employing an easily controlled electro-mechanical pump system. The artificial sphincter includes an inflatable cuff, a control pump fluidly coupled to the inflatable cuff, and an electro-mechanical pump system. The inflatable cuff is adapted to surround a urethra or rectum of the patient to facilitate continence. An inflation element or balloon can be included to further control pressure to the cuff.

7 Claims, 11 Drawing Sheets

(56) References Cited

U.S. PATENT DOCUMENTS

| | | | | |
|---|---|---|---|---|
| 4,222,377 | A | * | 9/1980 | Burton ............... A61F 2/004 128/DIG. 25 |
| 4,244,370 | A | | 1/1981 | Furlow et al. |
| 4,345,339 | A | | 8/1982 | Mueller et al. |
| 4,386,601 | A | * | 6/1983 | Trick ............... A61F 2/0027 128/DIG. 25 |
| 4,392,562 | A | | 7/1983 | Burton et al. |
| 4,411,260 | A | | 10/1983 | Koss et al. |
| 4,411,261 | A | | 10/1983 | Finney et al. |
| 4,437,457 | A | * | 3/1984 | Trick ............... A61F 2/004 128/DIG. 25 |
| 4,483,331 | A | | 11/1984 | Trick et al. |
| 4,517,967 | A | | 5/1985 | Timm et al. |
| 4,522,198 | A | | 6/1985 | Timm et al. |
| 4,541,420 | A | | 9/1985 | Timm et al. |
| 4,588,394 | A | | 5/1986 | Schulte et al. |
| 4,594,998 | A | | 6/1986 | Porter et al. |
| 4,619,251 | A | | 10/1986 | Helms et al. |
| 4,656,081 | A | | 4/1987 | Eiichi et al. |
| 4,665,902 | A | | 5/1987 | Goff et al. |
| 4,666,428 | A | | 5/1987 | Mattioli et al. |
| 4,669,456 | A | | 6/1987 | Masters et al. |
| 4,693,719 | A | | 9/1987 | Franko et al. |
| 4,699,128 | A | | 10/1987 | Hemmeter et al. |
| 4,881,531 | A | | 11/1989 | Timm et al. |
| 4,899,737 | A | | 2/1990 | Lazarian et al. |
| 5,050,592 | A | | 9/1991 | Olmedo et al. |
| 5,078,676 | A | * | 1/1992 | Bailly ............... A61F 2/004 128/DIG. 25 |
| 5,176,708 | A | | 1/1993 | Frey et al. |
| 5,283,390 | A | | 2/1994 | Hubis et al. |
| 5,445,594 | A | | 8/1995 | Elist et al. |
| 5,509,891 | A | | 4/1996 | Deridder et al. |
| 5,512,033 | A | | 4/1996 | Westrum et al. |
| 5,553,379 | A | | 9/1996 | Westrum et al. |
| 5,893,826 | A | * | 4/1999 | Salama ............... A61F 2/004 600/31 |
| 5,899,849 | A | | 5/1999 | Elist et al. |
| 6,346,492 | B1 | | 2/2002 | Koyfman |
| 6,579,230 | B2 | | 6/2003 | Yachia et al. |
| 6,600,108 | B1 | | 7/2003 | Wijnberg et al. |
| 6,953,429 | B2 | | 10/2005 | Forsell et al. |
| 7,481,763 | B2 | | 1/2009 | Hassler et al. |
| 2002/0111530 | A1 | * | 8/2002 | Bakane ............... A61F 2/0022 600/30 |
| 2003/0144648 | A1 | * | 7/2003 | Forsell ............... A61F 2/004 604/544 |
| 2004/0098113 | A1 | | 5/2004 | Forsell et al. |
| 2005/0014993 | A1 | | 1/2005 | Mische et al. |
| 2005/0267500 | A1 | * | 12/2005 | Hassler ............... A61F 5/0003 606/157 |
| 2008/0103353 | A1 | | 5/2008 | Jahns et al. |
| 2009/0105818 | A1 | | 4/2009 | George et al. |
| 2009/0171375 | A1 | * | 7/2009 | Coe ............... A61F 5/0059 606/151 |
| 2010/0185049 | A1 | * | 7/2010 | Birk ............... A61F 5/003 600/37 |
| 2011/0201875 | A1 | | 8/2011 | Stroumpoulis et al. |
| 2011/0208229 | A1 | * | 8/2011 | Snow ............... A61F 5/003 606/192 |
| 2011/0306824 | A1 | * | 12/2011 | Perron ............... A61F 5/0053 600/37 |
| 2012/0003108 | A1 | * | 1/2012 | Ozaki ............... F04D 29/426 417/413.1 |
| 2015/0374906 | A1 | * | 12/2015 | Forsell ............... A61M 5/14526 600/31 |

FOREIGN PATENT DOCUMENTS

| | | |
|---|---|---|
| GB | 2151484 A | 7/1985 |
| WO | 8601398 A1 | 3/1986 |
| WO | 9604865 A1 | 2/1996 |

OTHER PUBLICATIONS

Smith, "Management of Impending Penile Prosthesis Erosion with a Polytetrafluoroethylene Distal Wind Sock graft", Journal of Urology vol. 160, 1998, pp. 2037-2040.
Stein, et al., "Malleable Penile Prosthesis Removal Leaving Behind the Rear Tip Extenders: A Clinical Presentation", Urology International 50, 1993, pp. 119-120.
Wang, et al., "Hardness Evaluation of Penile Prostheses", International Journal of Urology 13,2006, pp. 569-572.
Yoo JJ, "Atala A. Catilage Rods as a Potential Material for Penile Reconstruction", Journal of Urology, discussion 1178, Sep. 1998, pp. 1164-1168.
Zerman, et al., "Penile Prosthetic Surgery in Neurologically Impaired Patients: Long-Term Follow-Up", Journal of Urology 175, 2006, pp. 1041-1044.
U.S. Appl. No. 13/328,856, filed Dec. 16, 2011, Allowed.
"Acu-Form Penile Prosthesis", Mentor, Aug. 1997, 1 page.
AMS Malleable 600 TM American Medical, 30915, 1983.
"InhibiZone Antibiotic Surface Treatment, (AMS Brochure)", 2001, 4 pages.
"Mentor Alpha I Inflatable Penile Prosthesis (Brochure)", Jul. 1996, 2 pages.
"Mentor Alpha I The Results are In", Apr. 1997, 15 pages.
"Mentor New from Mentor Urology Alpha I Narrow-Base (Brochure)", 1996, 2 pages.
"Mentor Patent guide for Alpha I Inflatable Penile Implant (Brochure)", 1996, 2 pages.
"Mentor Surgical Protocol Alpha I Inflatable Penile Implant (Brochure)", May 1998, 17 pages.
"mentor Urology Products", May 1998, 18 pages.
"Mentor Urology Products, (Brochure), Mentor", 1998, 20 pages.
"Parylene Micro Coating", AMS Brochure, 2000, 4 pages.
"Surgical Protocol, Mentor", Sep. 1997, 5 pages.
"The AMS Hydrflex Self-Contained Penile Prosthesis,", American Medical Systems Publication 50513, 1985.
"The Results are In Alpha I Setting High Standards for 3-Piece Inflatable Implants", Mentor Advertisement, 15 pages.
"Ultrex Plus Penile Prosthesis (AMS Advertisement)", 1992, 1 page.
AMS (Brochure) 700 Series Tactile, 2004, 2 pages.
AMS (Brochure) Ultrex/Ultrex Plus, 1998, 10 pages.
AMS 700 CX Penile Prosthesis (Brochure), 1999, 2 pages.
AMS Ambicor Penile Prosthesis (Brochure), 1996.
AMS 700 Inflatable Penile Prosthesis Product Line, 1992, 45 pages.
Anafarta, "Clinical Experience with Inflatable and Malleable Penile Implants in 104 Patients", Journal of Urology Int. 56, 1996, pp. 100-104.
Al-Najar, A., et al., "Should being aged over 70 years hinder penile prosthesis implantation?", BJU International, 2009, pp. 1-4.
Akin-Olugbade, et al., "Determinants of Patient Satisfaction Following Penile Prosthesis Surgery", J Sex Med, vol. 3,, 2006, pp. 743-748.
Abouassaly, et al., "Antibiotic-Coated Medical Devices: With an Emphasis on Inflatable Penile Prosthesis", Asian J Androl., vol. 6, Sep. 2004, pp. 249-257.
Agrawal, et al., "An Audit of Implanted Penile Prosthesis in the UK", BJU International, 2006, pp. 393-395.
Akand, "Mechanical Failure with Malleable Penile Prosthesis", Journal of Urology, vol. 70, No. 5, 2007, pp. e11-e12.
Benson RC Jr, et al., "Long-term results with the Jonas malleable penile prosthesis", Journal of Urology, 195, 134(5), November, pp. 899-901.
Burns-Cox N., "Fifteen-Years-Experience of Penile Prosthesis Insertion", International Journal Impotence Res. 9, 1997, pp. 211-216.
Candela J., et al., "Three-piece inflatable penile prosthesis implantation", J La State Med Society 148, 1996, pp. 296-301.
Chang, et al., "Penile Prosthesis Implantation", Retrieved from http://www.emedicine.com/med/to_Qic3047.htm, 2003, 19 pages.
Chiang, "10 Years Experience with Penile Prosthesis Implantation in Taiwanese Patients", Journal of Urology vol. 163, 2000, pp. 476-480.

(56) References Cited

OTHER PUBLICATIONS

Choi, "Ten Years of Experience with Various Penile Prosthesis in Korean, Yasei Medical", Journal vol. 35, No. 2, 1994, pp. 209-217.
Delk, "Early Experience with the American Medical Systems New Tactile Pump: Results of a Multicenter Study", Journal Sex Med 2, 2005, pp. 266-271.
Durazi Mohammed, et al., "Penile Prosthesis Implantation for Treatment of Postpriapism erectile Sysfunction", Urol. Journal. 5,2008, pp. 115-119.
Dsitch J., et al., "Long Term Mechanical Reliabiity of AMS 700 Series Inflatable Penile Prostheses: Cpmparison", Journal of Urology 158, Oct. 1997, pp. 1400-1402.
Dorflinger T., et al., "AMS Malleable Penile Prosthesis", Urology 28, No. 6, Dec. 1986, pp. 480-485.
Deuk Choi, et al., "Mechanical Reliability of the AMS 700 CXM Inflatable Penile Prosthesis for the Treatment of Male Erectile Dysfunction", Journal of Urology 168, Mar. 2001, pp. 822-824.
Deveci, et al., "Penile Length Alterations following Penile Prosthesis Surgery", European Urol. 51, 2007, pp. 1128-1131.
Fathy, "Experience with tube (Promedon Malleable Penile Implant)", Urol. Int. 79, 2007, pp. 244-247.
Fergltson, "Prospective Long-Term Resultsand Quality-of-Life-Assessment After Dura-II Penile Prosthesis Placement", Ural. 61(2), 2003, pp. 437-441.
Fogarty, "Cutaneous Temperature Measurements in Men with Penile Prosthesis: A Comparison Study", International Journal of Impotence Res. 17, 2005, pp. 506-509.
Garber, "Inflatable penile prostheses for the treatment of erectile dysfunction", Exper Rev. Med. Devices 2(3), 2005, pp. 341-350.
Gefen A., et al., "A biomechanical model of Peyronie's disease", Journal Biomech. 33, 2000, pp. 1739-1744.
Gefen, et al., "Optimization of Design and Surgical Positioning of Inflatable Penile Prostheses", Annals of Biomed. Eng 28, 2000, pp. 619-628.
Gefen, "Stresses in the normal and diabetic human penis following implantation of an inflatable prosthesis", Med. Biol. Eng. Comput. 37, 1999, pp. 625-631.
Gregory J., et al., "The Inflatable Penile Prosthesis: Failure of the Rear Tip Extender in reducing the incidence of Cylinder Leakage", Journal of Urology vol. 131, 1984, pp. 668-669.
Hellstrom, "Three-piece inflatable penile prosthesis components (surgical pearls on reservoirs, pumps, and rear-tip extenders)". International Journal of Impotence Research 15, Suppl 5, 2003, pp. S136-S138.
Henry G, "Advances in Penile Prosthesis Design", Current Sexual Health Reports 4, 2007, pp. 15-19.
Henry G., "Updates in Inflatable Penile Prostheses", Ural Clin N Am 34, 2007, pp. 535-547.
Jonas U. , "Silicone-Silver Penis Prosthesis (Jonas-Eska), Long-Term Reconstruction", Journal of Urology 160 (3 Pt 2), Sep. 1998, pp. 1164-1168.
Joseph D., et al., "Bilateral Dislocating of Rear Tip Extenders from the Inflatable Penile Prosthesis", Journal of Urology 128, Dec. 1982, pp. 1317-1318.
Kim, "Mechanical Reliability of AMS Hydraulic Penile Prostheses", Journal of Korean Medical Science 10(6), Dec. 1995, pp. 422-425.
Kadioglua., et al., "Surgical Treatment of Peyronie's Disease: A Critical Analysis", European Urology 50, 2006, pp. 235-248.
Kardar, "An Unusual Complication of Penile Prosthesis Following Urethroplasty", Scand. Journal of Urology Nephrol. 36, 2002, pp. 89-90.
Kaufman, "Use of Implantable Prostheses for the Treatment of Urinary Incontinence and Impotence", Am J. Surg. 130(2), Aug. 1975, pp. 244-250.
Kava, et al., "Efficacy and Patient Satisfaction Associated with Penile Prosthesis".
Khoudary, "Design Considerations in Penile Prostheses: The Medical Systems Product Line", Journal Long-Term Effects of medical Implants 7(1), 1997, pp. 55-64.

Krauss, "Use of the Malleable Penile Prosthesis in the Treatment of Erectile Dysfunction: A Prospective", Study of Postoperative journal of Urology vol. 142, 1989, pp. 988-991.
Kimoto, et al., "JSSM Guidleines for Erectile Dysfunction", International journal of Urology 15, 2008, pp. 564-576.
Lux, et al., "Outcomes and Satisfaction Rates for the Redesigned 2-Piece Penile Prosthesis", Journal of Urology vol. 177, Jan. 2007, pp. 262-266.
Lazarou, et al., "Technical Advances in Penile Prostheses", Journal Long-Term Effects of Medical impotency 16(3), 2006, pp. 253-247.
Leriche, et al., "Long-Term Outcome of Forearm Flee-Flap Phalloplasy in the Treatment of Transexualism", BJU International, 2008, pp. 1297-1300.
Levine, et al., "Mechanical Reliability and Safety of, and Patient Satisfaction With the Ambicor Inflatable Penile Prosthesis: Results of a 2 Center Study", Journal of Urology vol. 166, Sep. 2001, pp. 932-937.
Lumen, "Phalloplasty: A Valuable Treatment for Males with Penile Insufficiency", Journal of Urology 71(2), 2008, pp. 272-276.
Minervini, "Outcome of Penile Prosthesis Implantation for Treating Erectile Dysfunction: Experience with 504 Procedures", BJU International 97, 2005, pp. 129-133.
Malloy, et al., "Improved Mechanical Survival with Revised Model Inflatable Penile Prosthesis Using Rear-Tip Extenders", Journal of Urology 128, Sep. 1982, pp. 489-491.
Maul, "Experience with the AMS 600 Malleable Penile Prosthesis", Journal of Urology—931, 1986, pp. 135-929.
Merino, "Penile Prosthesis for the treatment of erectile dysfunction", Actas Urology Esp. 30(2), 2006, pp. 159-169.
Merino, "Penile Prosthesis for the Treatment of Erectile Dysfunction,", Aetas Urology Esp. 30(2), 2006, pp. 159-169.
Montague, et al., "Future consideration's: advances in the surgical management of erectile dysfunction", International Journal of Impotence Res. 12, Suppl. 4, 2000, pp. S140-S143.
Montague, et al., "AMS 3-Pieceinfiatable Penile Prosthesis Implantation in-Men with Peyronie's Disease: Comparison of Cx and Ultrex Cylinders", Journal of Urology 156, Nov. 1996, pp. 1633-1635.
Montague, "Clinical Guidelines Panel on Erectile Dysfunction: Summary Report on the Treatment of Organic Erectile Dysfunction", Journal of Urology 156, 1996, pp. 2007-2011.
Montague, "Contemporary Aspects of Penile Prosthesis Implantation", Urology International 70, 2003, pp. 141-146.
Montague, "Current Status of Penile Prosthesis implantation", Urology Reports 1, 2000, pp. 291-296.
Montague, "Cylinder Sizing: less is more", International Journal of Impotence Research 15, Suppl 5, 2003, pp. S132-S133.
Montague, "Early Experience with the Controlled Girth and Length Expanding Cylinder of the American Medical System Ultrex Penile Prosthesis", Journal of Urology 148, Nov. 1992, pp. 1444-1446.
Montague, "Experience with Semirigid Rod and Inflatavle Penile Prostheses", Journal of Urology 129, 1983, pp. 967-968.
Montague, "Penile Prosthesis Implantation For End-stage Erectile Dysfunction After Radical Prostatectomy", Reviews in Urology vol. 7 Suppl 2, 2005, pp. S51-S57.
Montague, "Penile Prosthesis Implantation", 1994, pp. 712-719.
Montague, "Surgical Approaches for Penile Prostheses Implantation: Penoscrotal VS Infrapubic", International Journal of Impotence Res. 15, Suppl 5, 2003, pp. S134-S135.
Montague, et al., "Penile Prosthesis Infections", International Journal of Impotence research 13, 2001, pp. 326-328.
Mulcahy, "Distal Corporoplasty for Lateral Extrusion of Penile prosthesis Cylinders", Journal of Urology vol. 161, Jan. 1999, pp. 193-195.
Mooreville, et al., "implantation of Inflatable Penile Prosthesis in Patients with Severe Corporeal fibrosis: Introduction of a New Penile Cavernotome", Journal of Urology 162, Dec. 1999, pp. 2054-2057.
Morey, et al., "Immediate Insertion of a Semirigid Penile Prosthesis for Refractory Ischemic Priapism", Military Medicine 172, 2007, pp. 11:1211.
Moul, "Experience With The Ams 600 Malleable Penile Prosthesis", Journal of Urology 135, 1986, pp. 929-931.

(56) References Cited

OTHER PUBLICATIONS

Mulcahy, "Another Look at the Role of Penile Prostheses in the Manangement of Impotence", Urology Annual 11, 1997, pp. 169-185.

Murphy, et al., "Failure of the Ambicors inflatable penile prosthesis to deflate", International Journal of Impotence Research 17, 2005, pp. 291-292.

Natali, et al., "Penile Implantation in Europe: Successes and Complications with 253 Implants in Italy and Germany", Journal of Sex Medicine 5, 2008, pp. 1503-1512.

Pearman, "Insertion of a Silastic Penile Prosthesis for the Teatment of Organic sexual Impotency", Journal of Urology 107(5), 1972, pp. 802-806.

Parulkar, "Revision.Surgery for Penile Implants", International Journal of Impotence 6, 1994, pp. 17-23.

Randrup, "Penile Implant Surgery: Rear Tip Extender That Stays Behind", Urology 34, 1992, pp. 1-87.

Rhee, "Technique for Concomitant Implantation of the Penile Prosthesis with the Male Sling", Journal of Urology 173, 2006, pp. 925-927.

Simmons, et al., "Penile Prosthesis Implantation: Past, Present And Future", International Journal of Impotence 20, 2008, pp. 437-444.

Sadeghi-Nejad, "Penile Prosthesis Surgery: A Review of Prosthetic Devices and Associated Complications", Journal of Sex Medicine 4, 2007, pp. 296-309.

Salama, "Satisfaction with the Malleable Penile Prosthesis Among Couples from the Middle East: Is it Different", International Journal of Impotence 16, 2004, pp. 175-180.

Scarzella, et al., "Use of Ambicor Penile Prosthesis in Peyronie's Disease and as Replacement for Malfunctioning AMS 700 Devices", J Sex Med, Suppl 1, 2004.

Small, "SmallOCarr on Penile Prosthesis: A Report on 160 Cases and Review of the Literature", Journal of Urology vol. 167, pp. 2357-2360.

* cited by examiner

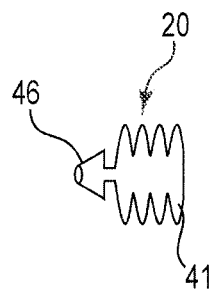
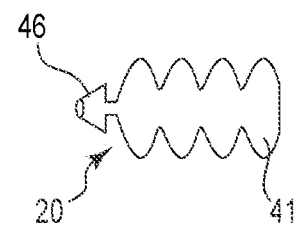
Fig. 6B          Fig. 6A
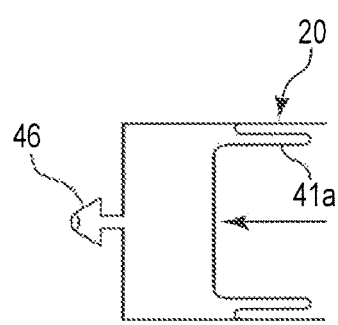
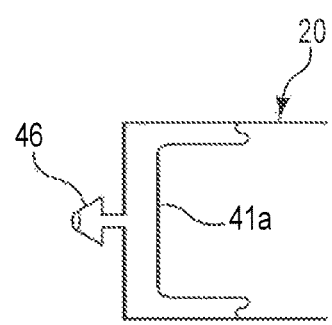
Fig. 6D          Fig. 6C

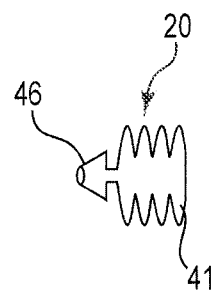
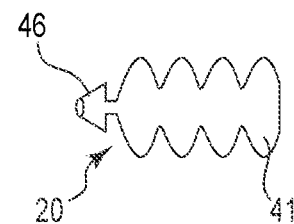
FIG. 34B   FIG. 34A
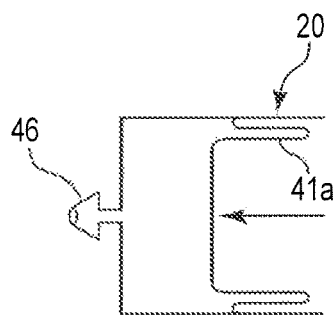
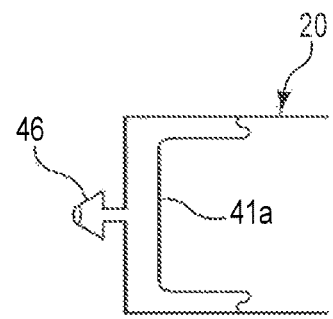
FIG. 35B   FIG. 35A

ARTIFICIAL SPHINCTER SYSTEM AND METHOD

CROSS-REFERENCE TO RELATED APPLICATIONS

This application is a Continuation of, and claims priority to, U.S. patent application Ser. No. 13/328,856, filed on Dec. 16, 2011, entitled "ARTIFICIAL SPHINCTER SYSTEM AND METHOD", which, in turn, claims priority to U.S. Patent Application No. 61/423,777, filed on Dec. 16, 2010, entitled "ARTIFICIAL SPHINCTER SYSTEM AND METHOD", the disclosures of which are incorporated by reference herein in their entirety.

FIELD OF THE INVENTION

The present invention relates generally to treatment of pelvic disorders and, more particularly, to an electro-mechanical artificial urinary sphincter system activated by a remote control, implanted switch or like device.

BACKGROUND OF THE INVENTION

Incontinence is an affliction that prevents a patient from controlling waste elimination functions. As one might expect, this condition can be quite debilitating and embarrassing and may severely limit the patient's activities.

Various techniques exist for treating incontinence in patients. One such technique is surgical implantation of an artificial sphincter. One form of artificial sphincter includes an appropriately sized inflatable cuff that is positioned around either the urethra or the rectum, depending upon the nature of the incontinence. A control pump is fluidly coupled to the cuff and to a pressure-regulating balloon, both of which are positioned within the body of the patient. Under normal conditions, the cuff is inflated which causes a compression of the urethra or the rectum, thus preventing unintentional discharge. When so desired, the patient manually actuates the control pump. Fluid is then withdrawn from the cuff and forced into the pressure-regulating balloon. As this occurs, the cuff relaxes allowing the urethra or rectum to expand and open. At this point, normal waste elimination functions are permitted. The pressure-regulating balloon contains a volume of fluid that is maintained at a relatively high pressure. The control pump is provided with a fluid resistor that allows pressurized fluid to slowly return to the cuff causing it to automatically re-inflate.

While manually-operated pump systems in conventional artificial sphincters can be useful, the patient must grasp a pump that is implanted in his scrotum and squeeze the pump bulb several times in order to void. The process may be considered burdensome and cause the patient to feel self conscious or conspicuous in public. In addition, there may be issues with over-pumping, as well as inefficiencies associated with imprecise manual pump volumes. Further, it is possible that urethral tissue health can be compromised by continuous cuff pressure.

SUMMARY OF THE INVENTION

The present invention provides an artificial sphincter employing an easily controlled electro-mechanical pump system. The artificial sphincter includes an inflatable cuff, a control pump coupled to the inflatable cuff, and an electro-mechanical pump actuator coupled to the control pump. A balloon or inflation element can be included in various embodiments. The inflatable cuff is adapted to surround a urethra or rectum of the patient to control continence. Sensors, electronic control devices and remote actuation devices can be included with embodiments of the present invention. One or more valves can be included with embodiments to selectively control the fluid displacement and path.

Various embodiments can include a chamber system for the pump, including one or more actuators and one or more internal seal members to displace fluid within the chamber to control inflation or deflation of the cuff. Other embodiments can include an inflation element (e.g., pressure-regulating balloon) integrated with the pump device or system to control fluid displacement.

Certain embodiments can include a peristaltic or roller pump system, or a "squiggle" pump system, adapted for use with the artificial sphincter system to control fluid flow and distribution to and from the cuff and pump.

Still other embodiments can include a centrifugal or vane pump system to control inflation and deflation of the cuff.

BRIEF DESCRIPTION OF THE DRAWINGS

FIGS. 34A and 34B show schematic views of a portion of an electro-mechanical sphincter and pump system in accordance with various example embodiments.

FIGS. 35A and 35B show schematic views of a portion of an electro-mechanical sphincter and pump system in accordance with various example embodiments.

DETAILED DESCRIPTION OF PREFERRED EMBODIMENTS

Figure 1:
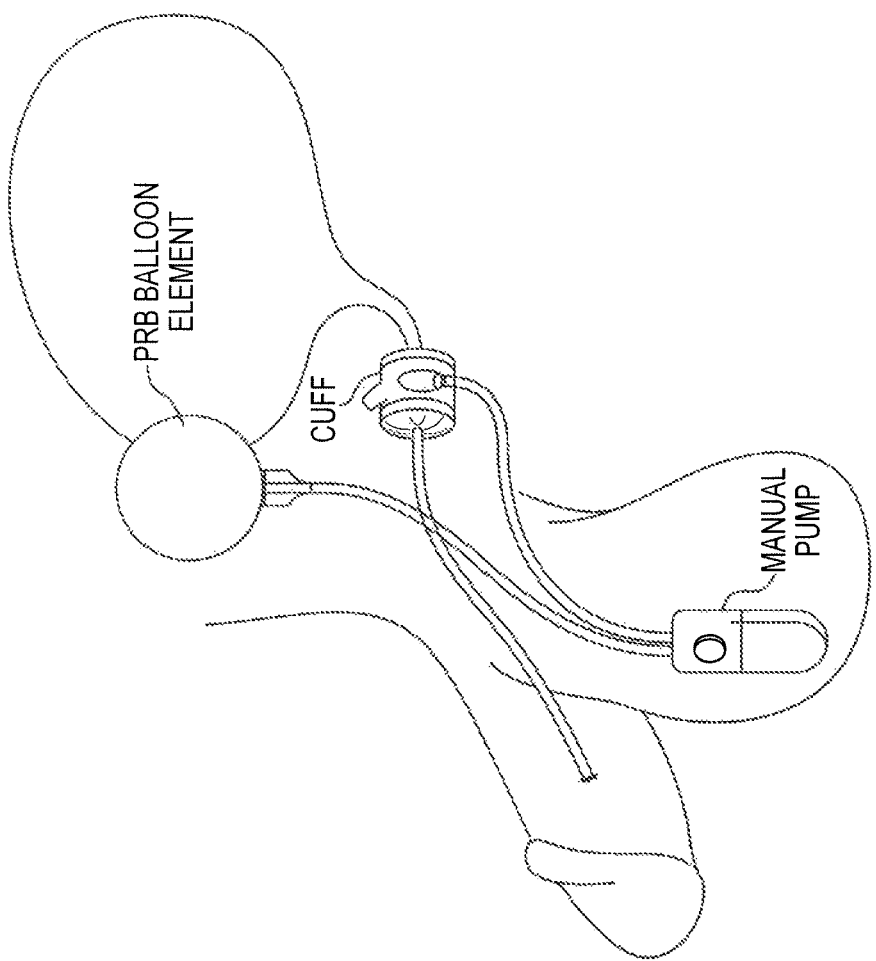
FIG. 1 shows an implanted conventional artificial sphincter system.
Figure 2:
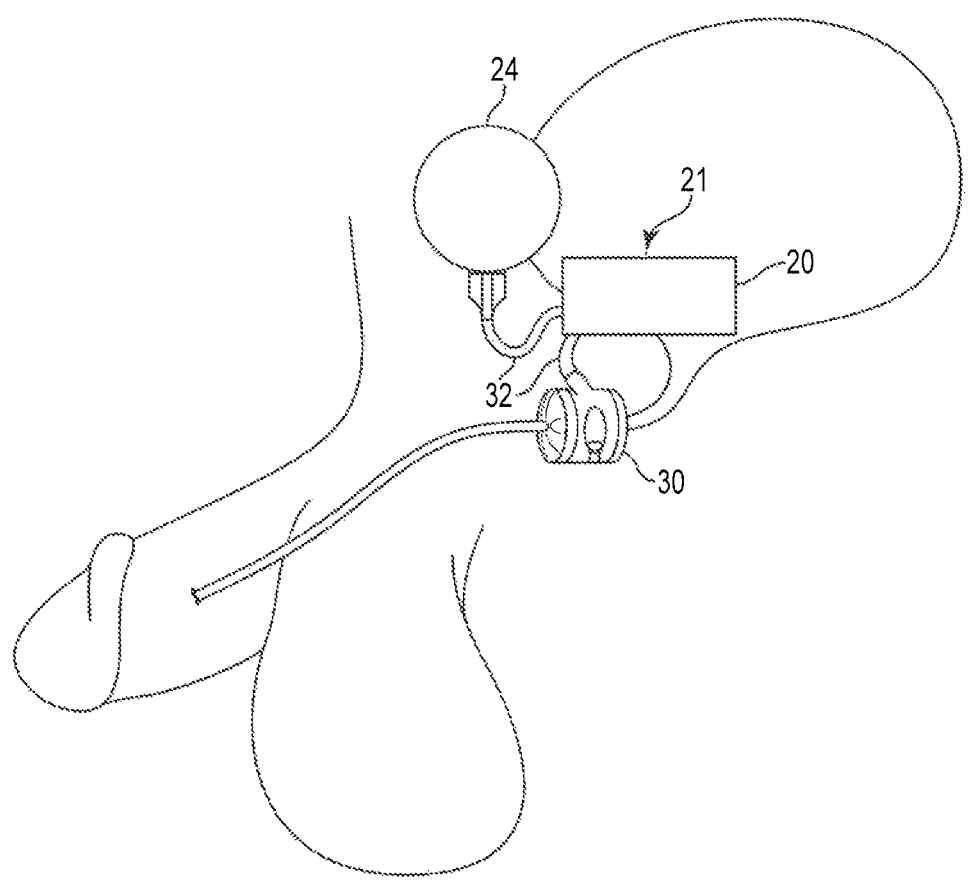
FIG. 2 shows an exemplary electro-mechanical artificial sphincter system implanted in accordance with embodiments of the present invention.
Figure 3:
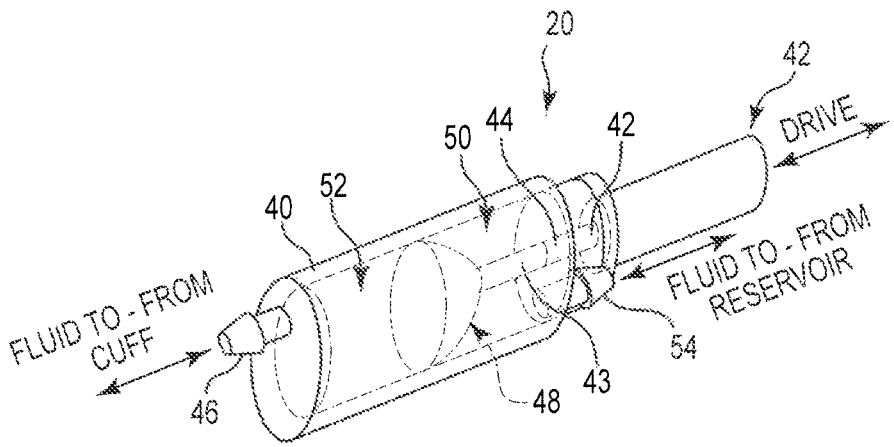
FIGS. 3-9 shows schematic views of portions of a linear actuated electromechanical sphincter and pump systems in accordance with embodiments of the present invention.

Referring generally to FIGS. 2-33, embodiments of the present invention can include an artificial sphincter system 10 adapted to control incontinence in the patient. In general, the cuff is attached to or wraps around a portion of the patient's urethra (or rectum) to control the sphinctering function of the particular anatomy.

The artificial urinary sphincter ("AUS") system 10 includes an electro-mechanical control pump 20 attached to a pressure-regulating inflation balloon or element 24. The inflation element 24 is likewise in operative fluid communication with the cuff 30 via one or more tubes or conduits 32, chambers, valves or similar structures. The various conduits 32 can be separable at connectors to facilitate the implantation during a surgical procedure. The inflation element 24 is constructed of polymer material that is capable of elastic deformation to reduce fluid volume within the inflation element 24 and push fluid out of the element 24 and into the cuff 30. However, the material of the element 24 can be biased or include a shape memory construct adapted to generally maintain the element 24 in its expanded state with a relatively constant fluid volume and pressure. In certain embodiments, this constant level of pressure exerted from the element 24 to the cuff 30 will keep the cuff at a desired inflated state when open fluid communication is provided between the element 24 and the cuff 30. This is largely due to the fact that only a small level of fluid displacement is required to inflate or deflate the cuff 30. Further, embodiments of the system 10 provide for implanting or placing the element 24 in the abdominal space. As such, stress events at this abdominal region (e.g., short increases in abdominal pressure) can be transmitted to measurably deform the element 24 to push fluid flow through to the cuff 30 to at least temporarily increase cuff 30 pressure to improve protection against stress incontinence. If the element 24 is located within the pump 20 or pump housing 21, the cuff 30 pressure can be dynamically controlled by the electronics, sensors and devices as disclosed herein. The sensors can monitor or 'listen' for stress events such as sudden movement, spike in abdominal pressure, neural or muscular electrical activity (e.g., reading electrical signals from leads like in an EMG device), and modulate device pressure to ensure the cuff 30 is at the optimal pressure at a given time or event, whether it is to void or to promote continence. The resting cuff 30 pressure can also be regulated by the electronics included with the pump 20 or pump housing 21. For instance, extra fluid aspirated from the cuff 30 can be stored in a passive fluid reservoir, such as the space inside a syringe-type pump system 20.

The cuff 30 may be formed from silicone, which has proven to be a reliable and medically safe material compatible with human tissue. The cuff 30 may also be formed from other suitably flexible biocompatible materials. The cuff 30 is positioned around the urethra within the patient's abdomen. Embodiments of the present invention can include, in whole or in part, the various components, devices, structures and techniques disclosed in U.S. Patent Publication Nos. 2010/0160716, 2010/0010530, 2006/0083848, U.S. Pat. Nos. 6,460,262, 7,011,622, 7,681,518, and PCT International Publication Nos. WO2001/060283, WO1993/004727, WO2006/041861 and WO2009/094431. Each of the above-listed patents and publications are incorporated herein by reference in their entireties. Further, the various components, devices, structures and techniques disclosed herein can be employed with, in whole or in part, known AMS 700 or AMS 800 sphincter devices and systems sold by American Medical Systems of Minnetonka, Minn.

Unlike pump systems used in conventional artificial sphincter systems, the system 10 and electro-mechanical pump 20 of the present invention can move fluid bidirectionally, automatically, or remotely without manual pumping. The flow can remain generally inactive or latched, and occasionally move a small but consistent volume. The flow can then reverse. Further, embodiments can include a housing 21 that comprises the pump 20 components, such as the motor and drive mechanisms, as well as the power (e.g., battery) and other electronic and mechanical components and elements disclosed herein.

Control over the pumps 20 in various embodiments can be facilitated remotely, by remotely triggering a switch and without manual manipulation like those required in conventional devices and systems. Namely, the pump 20 and motor can include a switch that is triggered to activate the motor. The activation can be used to trigger the pump to deflate the cuff 30 in certain embodiments to facilitate voiding, to release the cuff during sleep, etc. Other embodiments can use remote triggering to start the pump 20 to inflate or increase pressure from the cuff 30. The remote triggering of the pump 20, or other components of the system 10, can be included with portable small devices, such as watches, bands, key fobs, transmitter cases, and the like remote actuation or triggering devices. The remotes can communicate wirelessly with the system 10 controllers or electronics.

Embodiments of the pump 20 or housing 21 can include electric control or processing chips or electronics controllers in communication with the pump 20 and adapted to control the pump 20 and receive and store feedback data from the human body or the system 10 for later processing, or retrieval by a user or physician. Sensors, including those disclosed herein, can be included to automatically trigger the pump 20, e.g., to deflate or inflate the cuff 30 at proper moments or under certain stress events. One area where this is useful, is in detecting a desire to void. When a person wants to void, the pelvic floor and urethral sphincter muscles relax while the detruser (bladder muscle) contracts. For instance, one or more sensors can monitor electrical activity of the bladder or sphincter, or the pressure of the bladder and the abdomen, or other relevant inputs (e.g., an accelerometer device to gauge patient movement) to detect attempts by the patient to void such that the pump 20 can automatically deflate the cuff 30 at this appropriate time. Further, the controller electronics for the system 10, or pump 20, can be programmed and re-programmed (software or programmable chips) to deflate at a set time (e.g., night), or adjust cuff 30 pressure throughout the day to a schedule (e.g., increase cuff 30 pressure during known strenuous activity or times), or based on input from the sensors, to optimize continence.

Various component and chamber (e.g., syringe type) configurations of an embodiment of the system 10 and pump 20 are depicted in FIGS. 3-14. The pump 20 can include a chamber housing 40 and an actuator 42 (e.g., linearly driven) operably coupled to the chamber 40. The internal space of the chamber 40 is adapted to hold and displace fluid, e.g., liquid or gas. An input 44 to the chamber 40 is operably coupled with the actuator 42 and an output port 46 (e.g., distal to the actuator 42) provides connectivity to the cuff 30. Further within the chamber 40 is a fluid displacement member 48 operably connected to the actuator 42, such as via a shaft member 43, such that driving movement of the actuator 42 in and out of the chamber 40, relative to the displacement member 48, effects fluid displacement within the chamber 40. In certain embodiments, the member 48 is generally sealingly contacting inner walls of the chamber 40 such that a first chamber portion 50 is provided in front of the member 48, and a second chamber portion 52 is provided behind the member 48.

In certain embodiments, the member 48 is a moving piston-like or plunger-like (e.g., syringe) member adapted to travel, even if only a limited distance, within the chamber 40 via driving of the actuation member 48. In such cases, when the actuator 42 is driven into the chamber 40, the fluid present in the front chamber portion 50 will be displaced by the member 48 so that an amount of fluid will exit out the output port 46 to correspondingly inflate the cuff 30, to increase or stabilize continence. Similarly, retracting the actuator 42 and the member 48 will correspondingly increase the fluid in the first chamber portion 50, thereby reducing the fluid in the second chamber portion 52 and forcing excess fluid that was in that second chamber space to exit out a reservoir port 54 and into a balloon, pouch, chamber or like device or feature in communication with the second chamber portion 52 of the chamber 40. Retracting the actuator 42 will correspondingly deflate the cuff 30 to permit the patient to void.

For each embodiment disclosed herein, the actuator 42, or a portion of the member 48, can be biased to automatically, or selectively, return to the continence position where the cuff 30 is sufficiently inflated. Springs, shape memory materials (e.g., membrane 48), or even an automatic return motor or driver in the actuator can achieve this return to an inflatable home position for the pump 20 and cuff 30.

Figure 4:
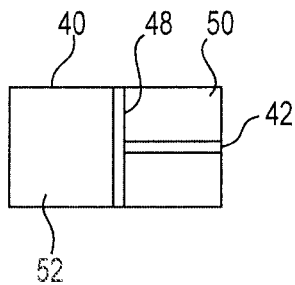
Figure 5:
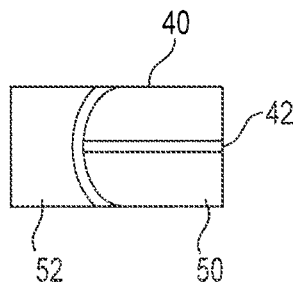
Figure 6:
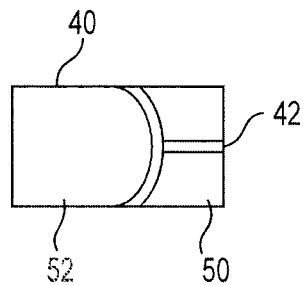

In various embodiments, as shown in FIGS. 3-7, the member 48 is a membrane member 48. The membrane member 48 is generally flexible, at least in part and can be substantially stationary with respect to linear movement within the chamber 40. Instead of driving back and forth in the chamber 40, the membrane member 48 deforms by expanding, bulging or contracting to displace fluid around it. As described herein, this displacement of fluid in the chamber portions 50, 52 will correspondingly move fluid in and out of the output port 46 and/or the reservoir port 54 to facilitate inflating or deflating the cuff 30. Again, a large level of fluid displacement is not required to drive fluid and pressure changes (e.g., through the output) to inflate or deflate the cuff 30 in the system 10, so this deformation of the membrane 48 can cause the desirable amount of fluid displacement. The membrane can be a cone or domed shaped member (FIGS. 3, 7) or a generally thin and flat member (FIGS. 4-6). FIGS. 4-6 depict the thin membrane 48 deforming outward (FIG. 5) from an initial rest position (FIG. 4) to displace fluid to inflate the cuff 30, and deforming inward (FIG. 6) to deflate the cuff 30, all according to the drive of the actuator 42 coupled to the membrane 40, or a portion thereof. In certain embodiments included within FIG. 3, the element 24 does not need to be included to maintain pressure in the cuff 30, but could be included as desired.

Various embodiment or the pump 20 itself can include a pump or chamber body portion 41 adapted to be collapsible, and expandable, to control fluid to and from the cuff 30. Such embodiments would not require a separate member 48 sealed within a chamber 40 as the chamber, or other portion of the pump 20, would essentially serve as the fluid transfer mechanism due to its construct. For instance, as shown in FIGS. 34A and 34B, the body 41 is constructed as a bellow or flexible wall configuration such that movement of the body 41 inward compresses the body 41 (FIG. 34B) to expel fluid through the port 46 and to the cuff 30 for inflation, or pressure increase. Likewise, retracting or pulling back on the body 41 (FIG. 34A) can draw fluid into the body 41 and out of the cuff 30 to facilitate deflation or emptying of the cuff 30. FIG. 34A can represent the body 41 in a neutral or resting home position. FIGS. 35A and 35B show another embodiment of such a body portion 41 having an internal bellow or like structure 41a adapted to selectively expand and contract with the pump 20 to drive fluid out the port 46 into the cuff 30, or from the cuff 30 back in.

Figure 7:
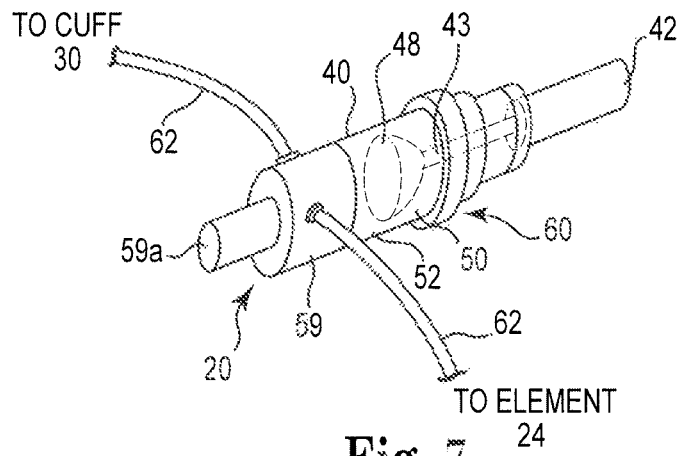
Figure 8:
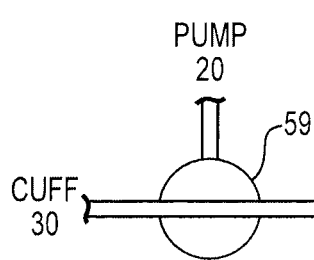
Figure 9:
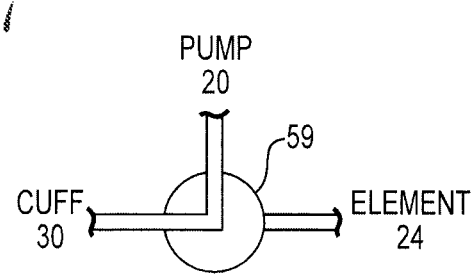
Figure 10:
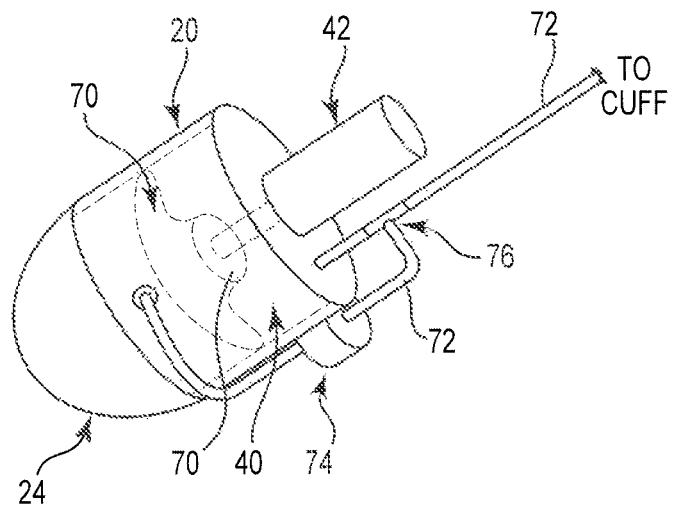
FIGS. 10-14 show schematic views of portions of a linear actuated electromechanical sphincter and pump system having an integrated pressure-regulating inflation element in accordance with embodiments of the present invention.

The embodiments of FIGS. 7-9 are similar to those of FIGS. 3-6, except they can include a 3-way valve 59 at the distal end of the pump 20 and an inflatable and deflatable member or tube element 60 (e.g., rather than a separate reservoir) wrapped around the chamber 40 proximate the actuator 42. The 3-way valve 59 is in operable fluid communication with the port 46 of the chamber 40, and the element 24 and the cuff 30 via a conduit 62 (or 32), or like fluid transfer member. Again, the member 48 can be a flexible membrane adapted to deform to displace fluid within the chamber 40, and chamber portions 50, 52 in particular, to control inflation and deflation of the cuff 30. FIG. 8 depicts a schematic representation of the valve 59 in an open position to permit open fluid communication between the element 24 and the cuff 30 along the conduits 62 and through the valve 59. The element 24 can maintain a constant inflating pressure for the cuff 30 in this operational position. FIG. 9 shows a schematic representation of the valve 59 triggered via a valve actuator 59a to provide open fluid communication between the cuff 30 and the pump 20 (not the element 24) to actively control the inflation and deflation of the cuff 30 via operation of the membrane 48 and the disclosed fluid displacement procedures. Like other triggering or actuation features and actions of embodiments of the present invention and system 10, the valve 59 can be triggered remotely via an electric signal, magnetic field, sensor activation, and the like.

Further, the actuators 42 disclosed herein can be driven in a myriad of ways, including, for example, linearly with an unwound electrical motor, a threaded power screw, a crank arm, or via like electric or electro-mechanical motor or driving means.

Various embodiments of the system 10 can include configurations where the pressure-regulating element 24 and pump 20 devices are combined or integrated, as shown in FIGS. 10-14. As such, a portion 70 of the element 24 extends into the chamber 40 of the pump 20 and into operable communication with the actuator 42. The actuator 42 can disrupt or otherwise move fluid within or out of the element 24. The element 24 is in operable fluid communication with the cuff 30 via one or more tubing or conduit elements 72. The elements 72 can also be provided in operable fluid communication with the inner space of the chamber 40, with a 2-way or like valve 74 included along a portion of the conduit 72 length to control fluid flow between the element 24, the cuff 30 and the chamber 40. Such a configuration is shown in one embodiment as a tee-connection 76.

Figure 11:
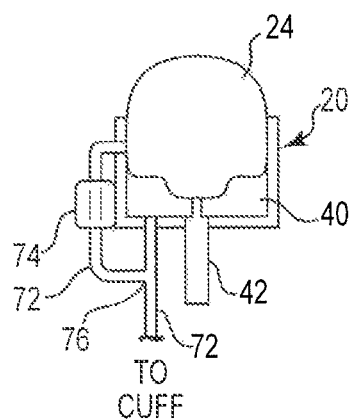
Figure 12:
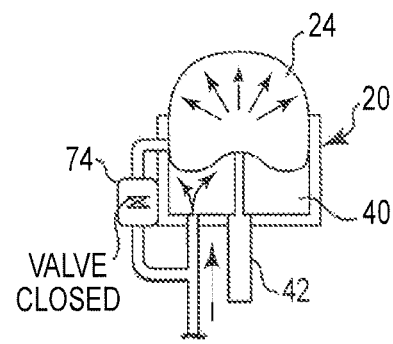
Figure 13:
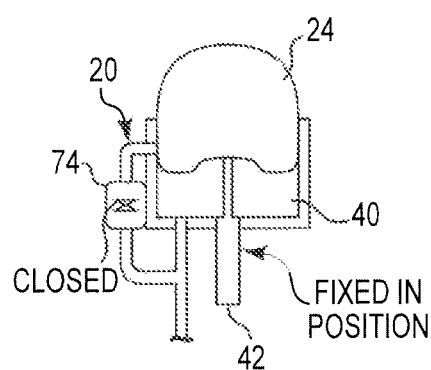
Figure 14:
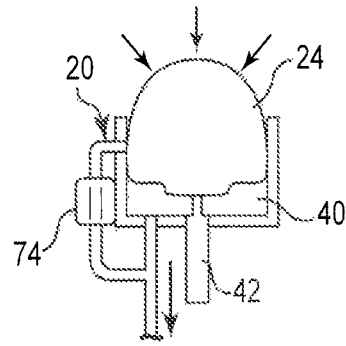
Figure 15:
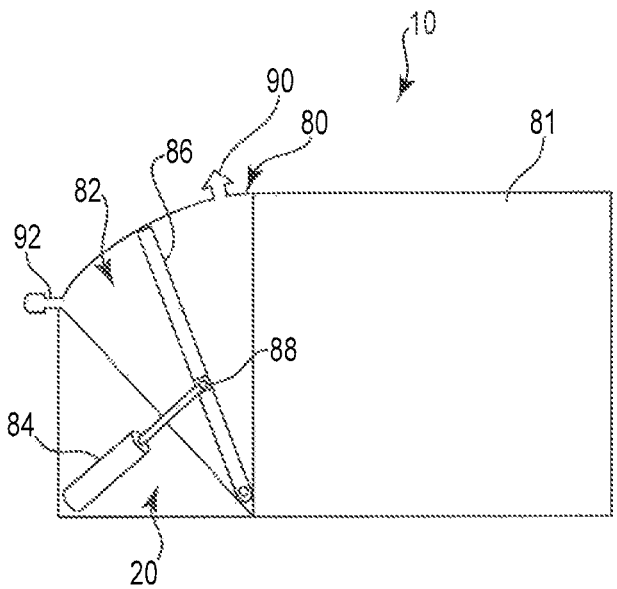
FIGS. 15-18 show schematic views of an electro-mechanical sphincter and pump system having a pivoting member in accordance with embodiments of the present invention.

As shown in FIG. 11, the active continence configuration for this system 10 has the valve 74 open to maintain the pressure in the cuff 30 at an inflated state. When the patient or user wishes to void, they begin the process by actuating the valve 74 (e.g., remotely or via sensors) to close the valve 74 such that fluid from the cuff 30 is directed into the chamber 40 to displace the element 24 and at least partially deflate the cuff 30, as shown in FIG. 12. Upon reaching a predefined or balance configuration with the valve 74 closed and increased fluid in the chamber 40, the actuator 42 is generally configured to be fixed in position until the voiding is complete (FIG. 13). Upon completion of the voiding, the valve 74 is opened and the actuator 42 is initiated to drive downward away from the pump 20 to bring the element 24 configuration into its continence position with fluid flow and pressure regulation complete between the element 24 and the inflated cuff 30.

FIGS. 15-18 depict another embodiment of the system 10. This embodiment can include a single-stroke or like pump 20. While any of the embodiments disclosed herein can be provided in a small or thin box-like configuration to house the pump, chamber, conduits, electronics, etc., this embodiment is particularly shown with such a configuration. A portion 80 (e.g., rounded corner portion) can include the pump 20 structures and components, including a fluid chamber 82. The other portion 81 of the system 10 can house the battery and electronics (e.g., for remote actuation, motor driving power, etc.).

Figure 16:
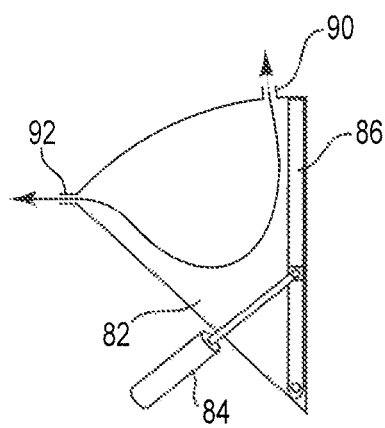
Figure 17:
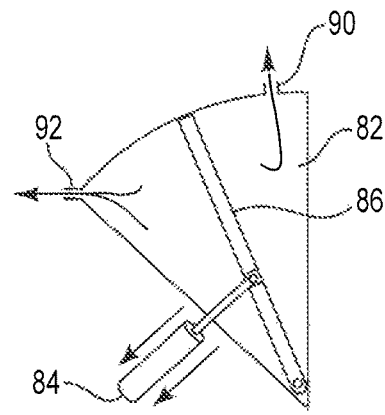
Figure 18:
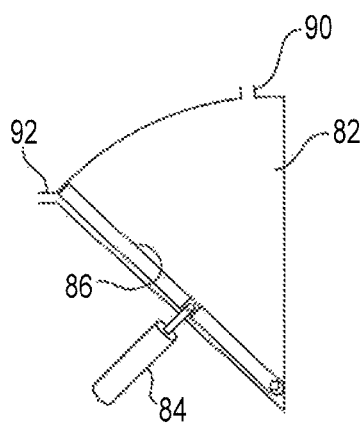

An actuator 84 (e.g., linear) can drive a member or pivoting wiper arm 86 (e.g., angular). The arm 86 can be rubberized, or of a like construct, and in sealing contact with various interior walls of the chamber 82. The actuator 84 is connected to the arm 86 at joint 88. The chamber 82 can include a cuff port 90 providing connection and operable fluid communication between the chamber 82 and the cuff 30. The chamber 82 can further include a balloon port 92 providing connection and operable fluid communication between the chamber 82 and the element 24. In the normal continence state, as shown in FIG. 16, the arm 86 is generally to one side of the chamber 82 such that free fluid flow is permitted between the element 24, the interior space of the chamber 82 and the cuff 30, to maintain an inflated cuff 30. To void, the actuator 84 is initiated to drive the arm 86 back into the chamber 82 space to at least substantially block off the fluid flow from the cuff 30 to the element 24, pulling fluid from the cuff 30 and pushing fluid into the element 24, thereby deflating the cuff 30 and permitting voiding, as shown in FIG. 17. In the deactivated or voiding configuration of FIG. 18, with the cuff 30 empty or deflated, the arm 86 has been pivoted to the side of the chamber 82 to sealingly block the port 92. A solenoid or other valve device can be employed to keep the fluid path between the chamber 82 and the element 24 closed for longer term deactivations. To return to the continence state, the actuator 84 drives the arm 86 back to the opposing side of the chamber 82 to permit open fluid flow between the cuff 30, the chamber 82 and the element 24, thereby inflating the cuff 30. Again, like the other embodiments, this mechanism can be powered by a power source, such as a battery, and actuated remotely by the user or patient.

Figure 19:
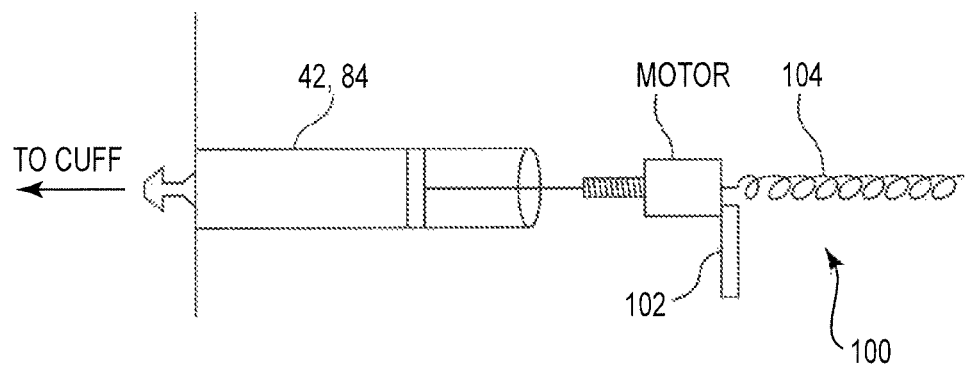
FIG. 19 shows a schematic view of a spring-driven override or release mechanism in accordance with embodiments of the present invention.
Figure 20:
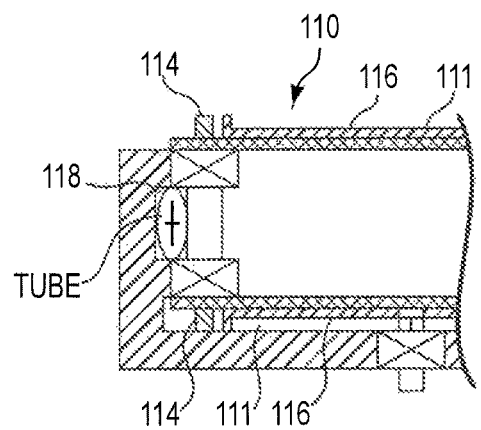
FIGS. 20-25 show schematic views of peristaltic or roller pump devices for electro-mechanical sphincter systems in accordance with embodiments of the present invention.

It is noted that any of the embodiments disclosed herein driven or controlled by electronics and power (e.g., battery), can include a safety or override mechanism to permit deflation of the cuff 30 even if their has been a failure or problem with any of the electronics, power or electro-mechanical structures or components. As shown in FIG. 19, a spring-driven mechanism 100 is provided, normally under tension, connected to any of the actuators (e.g., 42, 84) of the system 10 and capable of being triggered by an external safety magnet. When the magnet is held on the skin near the system 10, the magnetic field will actuate a mechanism release 102. As such, energy stored in a spring 104 of the mechanism 100 will be released to correspondingly release the normal system 10 actuator, thereby sucking or pulling fluid from the cuff 30. The spring 104 can be a normal spring device, or can be provided in other constructs, such as a flexible chamber walls, coated materials, etc. Further, other methods and devices for providing an override to provide an emergency release of the actuators or other structures to deflate or empty the cuff 30 are envisioned as well.

Figure 21:
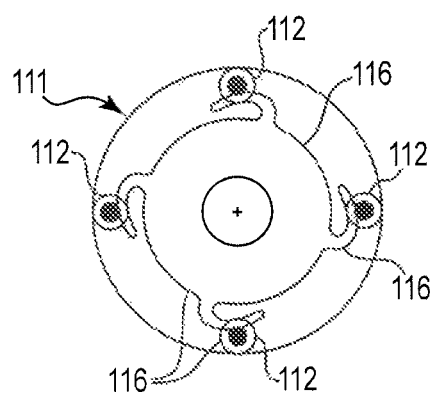

Various embodiments, as shown in FIGS. 20-25, can include a peristaltic or roller pump system 110 adapted for use with the systems 10. In general, the roller pump system 110 includes a roller 112, a roller shaft 114, spring loaded portions 116, and a tube channel 118. FIG. 21 shows the spring loading of the rollers 112 accomplished by a formed sheet metal spring, with the rollers 112 in a groove on a disk 111 to allow for relative motion, while still providing the bias of the spring 116 such that the roller is biased down into the tube channel 118. This configuration provides tube or conduit 120 occlusion, with the tube or conduit 120 running in a controlled depth on the ends of the spring-loaded rollers 112 in the tube channel 118, to control the amount of tube compression and corresponding occlusion. This pump system 110 can be self-contained to include a housing for the battery, control electronics, return reservoir 115 (or element 24), etc. The system 110 will include communication between the pump and the cuff 30, as well as the element 24 or return fluid reservoir 115. In general, the roller 112 can compress the tube or conduit 120 providing fluid to the cuff 30, extending within the tube channel 118, to control deflation of the cuff 30.

Figure 22:
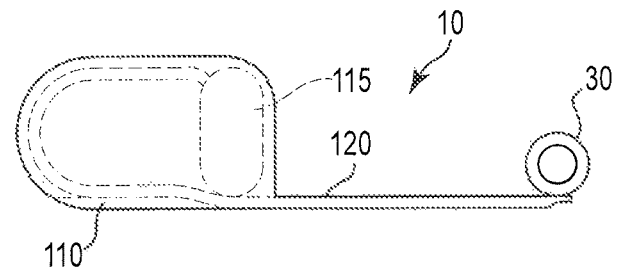
Figure 22A:
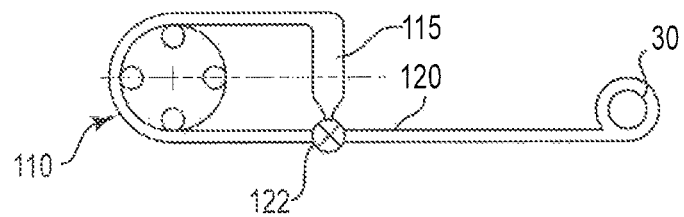
Figure 23:
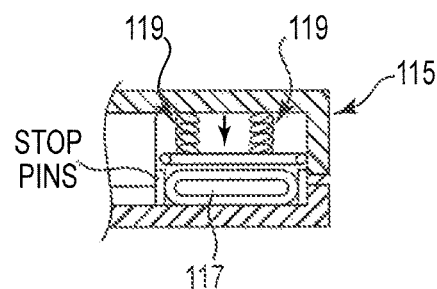

Embodiments of the pump system 110 shown in FIGS. 22-23 can include a 3-way valve 122 and a spring-loaded reservoir 115. The valve 122 is provided at the juncture of the pump 110, the reservoir 115 and the conduit 120 running to the cuff 30. The valve 122 selectively connects the cuff 30 to the pump 110 (fluid communication) to evacuate or deflate the cuff 30. To refill the cuff 30, the valve 122 provides fluid communication between the reservoir 115 and the cuff 30. Compression springs 119 in the reservoir portion 115 for this embodiment can bias the bladder 117 of the reservoir portion 115 such that it is generally pushing fluid to the cuff 30 when the valve 122 permits open communication between the reservoir 115 and the cuff 30.

Figure 24:
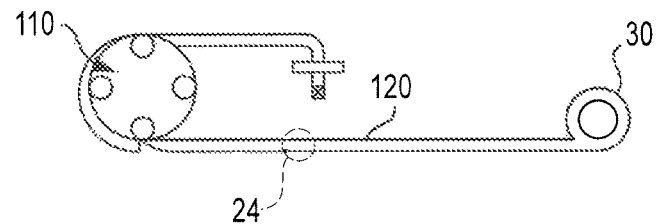

FIG. 24 shows an embodiment of the pump system 110 not having a valve or bladder (reservoir 115 or element 24). Instead, fluid is stored in the tubing 120 and the pump motor is reversed (uncompressing tubing 120) to refill the cuff 30. So voiding is enabled with compression on the tubing (by pump and roller) to evacuate the cuff 30. When a continence state is desired, the compression is released with reversal of the pump motor to enable fluid flow through the tubing 120 to again inflate the cuff 30. Alternative embodiments could put an element 24 (shown in phantom lines) in line with the cuff to provide constant fluid pressure or balance to the cuff 30. A vent and filter device 124 can be included in communication with the pump 110 to assist in controlling pressure and fluid within this system.

Figure 25:
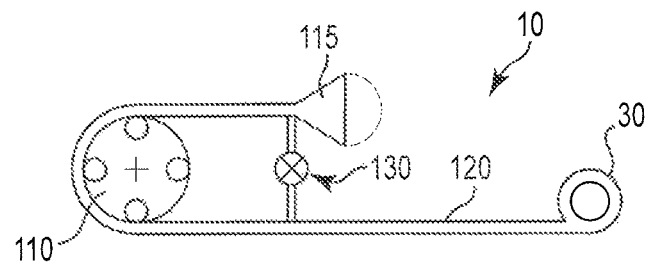

This roller pump system 110, like others disclosed herein, can include an override or bypass system or method to evacuate or deflate the cuff 30. As shown in FIG. 25, a bypass activated valve 130 (e.g., capable of being magnetically activated, externally activated) can be included in communication between the reservoir portion 115 and the cuff 30 and/or the tubing 120 to the cuff 30. The reservoir 115 is maintained in a negative pressure state such that activating the valve correspondingly bypasses the pump motor 110 to empty or deflate the cuff 30.

Figure 26:
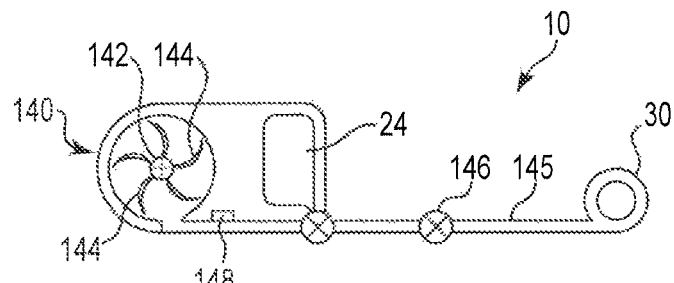
FIGS. 26-28 show schematic views of centrifugal or vane pump devices for electro-mechanical sphincter systems in accordance with embodiments of the present invention.
Figure 27:
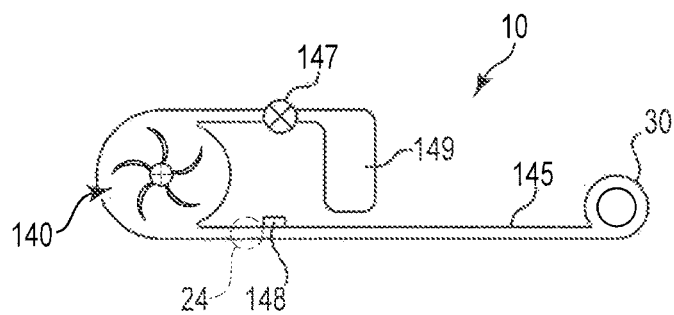
Figure 28:
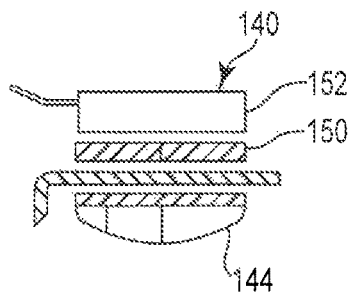
Figure 29:
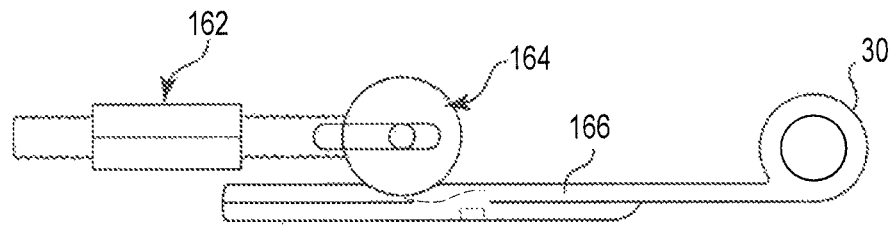
FIGS. 29-33 show schematic views of a 'squiggle' motor pump system for electromechanical sphincter systems in accordance with embodiments of the present invention.
Figure 30:
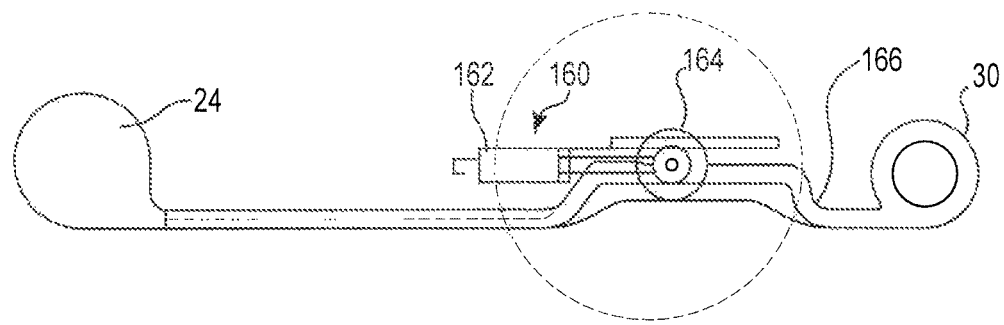

Various embodiments of the system 10 can include a centrifugal or vane pump system 140 to control inflation and deflation of the cuff 30, as shown in FIGS. 26-28. This pump system 140 can include a brushless DC motor 142 driving a rotating impeller 144 to transfer fluid out of the cuff 30. The pump 140 is spun up or initiated to create positive pressure in the cuff 30. The reservoir or element 24 is generally under negative pressure and can therefore be used to evacuate the cuff 30. Alternatively, the element 24, or other reservoir bladder or portions, can be included to pressurize or refill the cuff 30 similar to other embodiments disclosed herein.

A 2-way valve 146 can be included along tubing or conduit 145 (extending fluid communication to cuff 30) to trap pressure in the cuff 30. Further, a 3-way valve 148 can be included to selectively control fluid communication of conduits or lines between the pump 140, the reservoir 24 and the cuff 30. A pressure sensor 148 can be included as well to trigger or control the various components.

An embodiment of the pump system 140 for the invention 10 is provided in FIG. 27, including a reservoir bladder 149, and an element 24 in-line with the cuff 30 such that the reservoir 24 is under negative pressure to keep the cuff 30 inflated, or to refill the cuff 30. A 2-way valve 147 can be included to provide control over the fluid communication of the reservoir 149 and the motor 140, or cuff 30. Again, a pressure sensor can be included to provide additional control and detection of the fluid system.

In certain embodiments of the pump system 140, the pump impeller 144 can be magnetically coupled to the motor. As depicted, a magnet element 150 is positioned between the motor 152 and the magnet impeller 144 (e.g., magnet and impeller).

With any of the pump systems 140, the impeller 144 can be run in reverse to correspondingly reverse the fluid flow (e.g., inflate or deflate the cuff 30).

Figure 31:
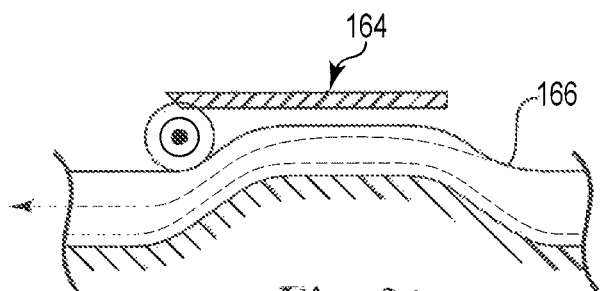
Figure 32:
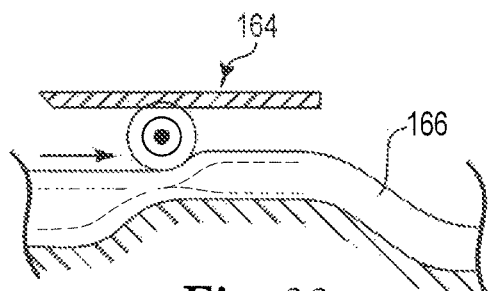
Figure 33:
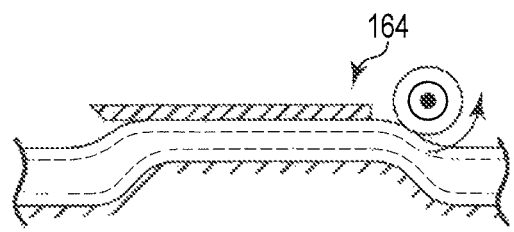

Embodiments of the system 10 are shown in FIGS. 29-33 including a "squiggle motor" pump system 160. Embodiments of this pump system 160 can implement pumps, mini- or mico-pumps or other "squiggle motor" systems or components sold by New Scale Technologies of Victor, N.Y. This system 160 for the present embodiment can be particularly useful in those systems disclosed herein having linear actuators for the pump systems. The system 160 can include a motor 162, a roller or bearing mechanism 164 and a tubing or conduit 166. Again, the tubing 166 provides fluid communication between the system 160 and the cuff 30. The system 160 has the advantage of not having moving seals, and being self-locking so that the motor does not need power to maintain pressure along the tubing 166. The motor 162 drives the bearing 164 along the tubing 166 to displace fluid relative to the cuff 30. For instance, the compression of the bearing 164 on the tubing 166 eventually cuts off or disrupts pressure to the cuff 30, thereby clearing or emptying the cuff 30. When fluid communication is not disrupted between the cuff 30 and the element 24, the cuff 30 remains under pressure and inflated at least partially due to the element 24. FIGS. 31-33 depict the operation of the squiggle motor pump system 160 engaging the tubing 166 (FIG. 31), compressing or pushing on the tubing 166 to close off (e.g., closing i.d. of tubing 166) the fluid flow (FIG. 32) to the cuff 30. This isolates the cuff 30 from the element 24. Once the roller clears (e.g., a cam surface) it returns or pops up so that the tubing 166 is again in open fluid communication with the cuff 30, and the element 24 can maintain the pressure of the inflated cuff 30. At the end of the process, the roller can automatically retract back to its starting position.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. An artificial sphincter system, comprising:
   an adjustable cuff adapted to apply pressure to a bladder neck or a urethra to promote continence;
   a pump configured for inflation or deflation of the cuff, the pump including;
      a fluid chamber in fluid communication with the cuff;
      a flexible membrane disposed within the fluid chamber, the flexible membrane dividing the fluid chamber into a first portion and a second portion, the flexible membrane being cone or dome shaped; and
      an actuator operatively coupled to the flexible membrane; and
   a valve in fluid communication with the fluid chamber, the cuff, and an inflation element,
   wherein the flexible membrane is disposed between the valve and the actuator,
   wherein when the valve is in a first position, the inflation element and the cuff are in fluid communication,
   wherein when the valve is in a second position, the fluid chamber and the cuff are in fluid communication.

2. The system of claim 1, wherein the pump further includes a motor adapted for remote actuation.

3. The system of claim 1, wherein the flexible membrane is configured to deform upon actuation of the pump to displace fluid within the fluid chamber.

4. The system of claim 1, wherein the inflation element is configured to receive excess fluid during deflation of the cuff.

5. The system of claim 1, further including a pump housing to house at least the pump.

6. The system of claim 1, wherein the pump is linearly driven.

7. The system of claim 1, wherein the flexible membrane is coupled to a sidewall of the fluid chamber.

* * * * *